United States Patent
Wang

(10) Patent No.: US 9,810,962 B1
(45) Date of Patent: Nov. 7, 2017

(54) ELECTROCHROMIC MATERIAL AND ANTI-DAZZLE MIRROR HAVING THE SAME

(71) Applicant: E-CHEM ENTERPRISE CORP., Taoyuan (TW)

(72) Inventor: Tzun-Wu Wang, Taoyuan (TW)

(73) Assignee: E-CHEM ENTERPRISE CORP. (TW)

( * ) Notice: Subject to any disclaimer, the term of this patent is extended or adjusted under 35 U.S.C. 154(b) by 0 days.

(21) Appl. No.: 15/245,175

(22) Filed: Aug. 24, 2016

(51) Int. Cl.
*G02F 1/15* (2006.01)
*B60R 1/08* (2006.01)
*C07D 213/53* (2006.01)
*G02F 1/157* (2006.01)
*G02F 1/1335* (2006.01)
*C09K 9/02* (2006.01)
*G02F 1/153* (2006.01)

(52) U.S. Cl.
CPC ............ *G02F 1/1521* (2013.01); *B60R 1/088* (2013.01); *C07D 213/53* (2013.01); *G02F 1/133553* (2013.01); *G02F 1/15* (2013.01); *G02F 1/157* (2013.01); *C09K 9/02* (2013.01); *G02F 1/153* (2013.01)

(58) Field of Classification Search
CPC ..... B60R 1/088; G02F 1/1506; G02F 1/1521; G02F 1/1525; G02F 1/157; G02F 2202/04; G02F 2202/10; G02F 1/33553; G02F 1/15; G02F 1/153; C09K 9/02; C09K 2211/1011; C09K 2211/1029; C07D 213/00; C07D 213/53; G02C 7/10; G02C 7/101

USPC ........ 359/265–267, 270, 273; 252/62.2, 582, 252/583, 586
See application file for complete search history.

(56) References Cited

U.S. PATENT DOCUMENTS

| | | | | |
|---|---|---|---|---|
| 5,169,953 A | * | 12/1992 | Mizuguchi | C09K 9/02 544/144 |
| 5,298,063 A | * | 3/1994 | Mizuguchi | C09K 9/02 106/31.64 |
| 6,023,364 A | * | 2/2000 | Kobayashi | B60R 1/088 359/265 |
| 6,538,792 B1 | * | 3/2003 | Kobayashi | C09K 9/02 252/582 |
| 7,633,668 B2 | * | 12/2009 | Das | C09K 9/02 252/583 |
| 8,519,150 B2 | * | 8/2013 | Kondou | C07D 495/04 252/586 |
| 2016/0231636 A1 | * | 8/2016 | Biver | C09K 9/02 |
| 2016/0282694 A1 | * | 9/2016 | Biver | C09K 9/02 |

* cited by examiner

*Primary Examiner* — Loha Ben

(57) ABSTRACT

Comparing to conventional electrochromic material showing a primary drawback of high manufacturing cost due to low synthetic yield, the inventors of the present invention modulate the chemical structure of a traditional viologen compounds so as to develop a novel electrochromic material performing an excellent advantage of low manufacturing cost resulted from high recovery rate. Moreover, differing from conventional electrochromic devices (ECD) installed with the conventional electrochromic material, the inventors of the present invention also propose an anti-dazzle mirror having the novel electrochromic material, wherein the proposed anti-dazzle mirror shows an outstanding reflectivity performance.

11 Claims, 3 Drawing Sheets

ELECTROCHROMIC MATERIAL AND ANTI-DAZZLE MIRROR HAVING THE SAME

BACKGROUND OF THE INVENTION

1. Field of the Invention

The present invention relates to the technology field of electroactive materials, and more particularly to an electrochromic material applied in anti-dazzle mirrors.

2. Description of the Prior Art

Electrochromism is a phenomenon displayed by electroactive materials of reversibly changing colour by using bursts of electric field to cause electrochemical redox reactions in the electrochromic materials. With the change of electrochromic material's energy level made by lectric field, the optical properties of the electrochromic material change reversibly in a wavelength range of visible light, such as transmittance, reflectivity or absorbance.

Electrochromic materials have been widely applied in smart window. By applying various voltages to the smart window, the transmittance and absorbance of the smart window for the visible light having a specific wavelength can be modulated, so as to adjust indoor temperature and illumination. Moreover, the electrochromic materials are also applied in sunroof and driving mirrors of automotive. Conventional electrochromic materials are classified into transition metal oxides, intercalated materials, organic compounds, and conductive polymers. In the four kinds of the electrochromic materials, the organic compounds and the conductive polymers gradually become mainstream application because of having some advantages including low manufacturing cost, simple manufacturing process, high conductivity, and abundance of colors.

Common organic compounds include methyl viologen, heptyl viologen and phenyl viologen having a viologen-based chemical structure represented by following three chemical formulas.

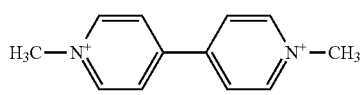

[chemical formula I]

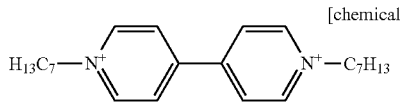

[chemical formula II]

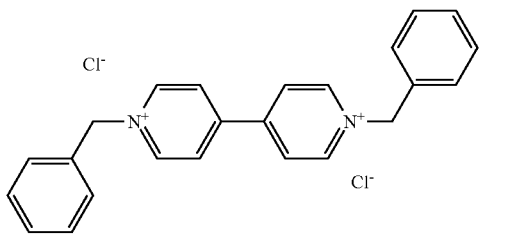

[chemical formula III]

Viologen-based material is colorless under a neutral state and shows blue purple colour under a reduction state. Because traditional viologen-based materials are sensitive to ultraviolet light, they are not suitable for being applied in driving mirrors of automotive. In view of that, a Taiwan invention with patent number of I265972 discloses an improved electrochromic material, which has a viologen-based chemical structure represented by following three chemical formula.

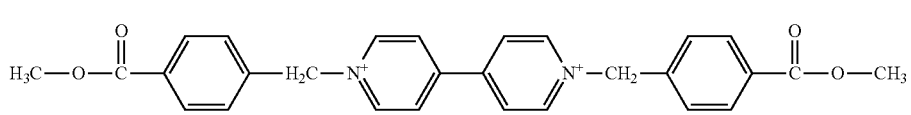

[chemical formula IV]

The improved electrochromic material represented by the chemical formula IV is 1,1-bis(4-methoxycarbonyl) benzyl-4,4'-bipyridinium tetrafluoroborate, and can be synthesized by using following manufacturing process steps:

step (1'): adding 1.7-gram 4,4'-bipyridine (0.01 mol) and 5-gram methyl (4-bromomethyl) benzoate (0.02 mol) into a first round-bottom flask;

step (2'): adding 30-milliliter cyanide methane into the first round-bottom flask, and then stirring the solution in the first round-bottom flask;

step (3'): rising the temperature of the solution in the first round-bottom flask up to a first reaction temperature of 85° C., and then keeping the first reaction temperature for 5 hours; after that, a semi-finished product is produced in first round-bottom flask by 60% yield, and the semi-finished product is 1,1-bis (4-methoxycarbonyl) benzyl-4,4'-bipyridinium dibromide;

step (4'): adding the semi-finished product into a second round-bottom flask, and then adding water into the second round-bottom flask for dissolving the semi-finished product; and step (5'): adding an aqueous solution of lithium tetrafluoroborate into the second round-bottom flask, and then maintaining the temperature of the solution in the second round-bottom flask at a second reaction temperature of 10° C.; after that, a product is produced in second round-bottom flask by 54% yield, and the product is 1,1-bis (4-methoxycarbonyl) benzyl-4,4'-bipyridinium tetrafluoroborate.

After obtaining the product of the improved electrochromic material disclosed by Taiwan patent number I265972, the electrochromic material is applied in an automotive mirror; moreover, the reflectivity and color changing speed of the automotive mirror is measured and recorded in following Table (1).

TABLE 1

| Measurement items | Results |
|---|---|
| Reflectivity obtained after changing electrochromic material's color | 8.5% |
| color changing speed (from 65% to 15%) | 2 s |
| color changing speed (from 15% to 65%) | 6 s |
| Reflectivity obtained after changing electrochromic material's color (measured after using xenon lamp to illuminate the automotive mirror for 500 hours) | 9.4% |
| Reflectivity obtained after changing electrochromic material's color (after treating the automotive mirror with 30000-time cycling test by DC 1.1 V) | 9.1% |

As engineers skilled in designing and manufacturing electrochromic materials know, although the improved electrochromic material disclosed by Taiwan patent number I265972 shows the advantages of high color changing speed and low reflectivity, the improved electrochromic material cannot be widely implemented in the automotive mirror due to its low synthetic yield. In view of that, inventors of the present application have made great efforts to make inventive research thereon and eventually provided an electrochromic material and an anti-dazzle mirror having the same.

SUMMARY OF THE INVENTION

A first objective of the present invention is to provide an electrochromic material. Comparing to a conventional electrochromic material showing a primary drawback of high manufacturing cost due to low synthetic yield, the inventors of the present invention modulate the chemical structure of a traditional viologen compounds so as to develop a novel electrochromic material performing an excellent advantage of low manufacturing cost resulted from high recovery rate.

In order to achieve the first objective of the present invention, the inventor of the present invention provides an embodiment for the electrochromic material, which is a viologen compound having a specific chemical structure represented by following chemical formula (1):

[chemical formula (1)]

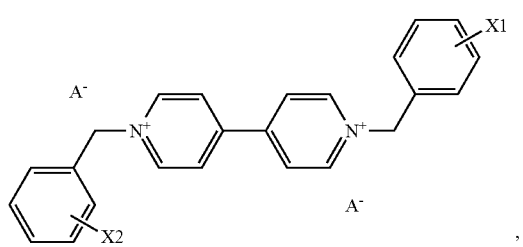

wherein both X1 and X2 in the chemical formula (1) are a halogen, and $A^-$ being a compensatory ion.

For the aforesaid embodiment for the electrochromic material, wherein the compensatory ion is selected from the group consisting of: $BF_4^-$, $PF_6^-$, $AsF_6^-$, $ClO_4^-$, $CH_3COO^-$, $CH_3(C_6H_4)SO_3^-$, and $(CF_3SO_2)_2N^-$.

A second objective of the present invention is to provide an anti-dazzle mirror having a novel electrochromic material. Differing from conventional electrochromic devices (ECD) having the conventional electrochromic material, the proposed anti-dazzle mirror having the novel electrochromic material particularly shows an outstanding reflectivity performance.

For achieving the second objective of the present invention, the inventor of the present invention provides an embodiment for the anti-dazzle mirror, comprising:
a mirror body, comprising:
   a first transparent layer;
   a first electrode layer, being disposed on the first transparent layer;
   an electrochromic layer, being disposed on the first electrode layer and comprising an electrochromic material;
   a second electrode layer, being disposed on the electrochromic layer;
   a second transparent layer, being disposed on the second electrode layer; and
   a reflective film, covering the second transparent layer, wherein the electrochromic material is viologen compound having a specific chemical structure represented by following chemical formula (1); in the chemical formula (1), both X1 and X2 are a halogen, and $A^-$ is a compensatory ion.

[chemical formula (1)]

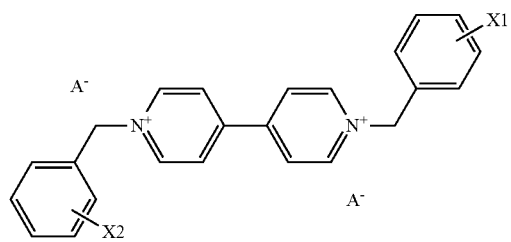

For the aforesaid embodiment for the anti-dazzle mirror, wherein a mirror frame is used for housing the mirror body.

For the aforesaid embodiment for the anti-dazzle mirror, wherein both the first transparent layer and the second transparent layer are selected from the group consisting of: transparent glass and transparent acrylic.

For the aforesaid embodiment for the anti-dazzle mirror, wherein the manufacturing material of the reflective film is selected from the group consisting of: aluminum (Al), silver (Ag), copper (Cu), chromium (Cr), and combinations thereof.

For the aforesaid embodiment for the anti-dazzle mirror, wherein a seal agent is used for making the first transparent layer disposed with the first electrode layer and the second transparent layer disposed with the second electrode layer attach to each other.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

To more clearly describe an electrochromic material and an anti-dazzle mirror having the electrochromic material according to the present invention, embodiments of the present invention will be described in detail with reference to the attached drawings hereinafter.

The present invention proposes an electrochromic material, which is a viologen compound having a specific chemical structure represented by following chemical formula (1), wherein both X1 and X2 in the chemical formula (1) are a halogen, and $A^-$ is a compensatory ion.

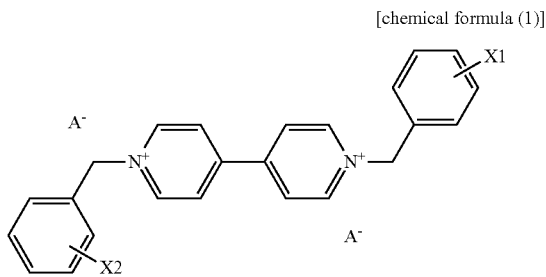

[chemical formula (1)]

It needs to further explain that, the said compensatory ion is selected from the group consisting of: $BF_4^-$, $PF_6^-$, $AsF_6^-$, $ClO_4^-$, $CH_3COO^-$, $CH_3(C_6H_4)SO_3^-$, and $(CF_3SO_2)_2N^-$. Moreover, the compensatory ion can also be a halogen ion. On the other hand, it is worth noting that the X1 and X2 can be two identical halogens or two different halogens.

EMBODIMENT

For proving the practicability of the novel electrochromic material proposed by the present invention, an exemplary synthesizing method for the electrochromic material will be introduced in follows. The synthesizing method mainly consists 6 manufacture processing steps of:

step (1): adding 0.1-mol 4,4'-bipyridine and 0.22-mol 3-fluorobenzyl bromide into a first round-bottom flask;

step (2): adding acetonitrile into the first round-bottom flask, and then stirring the solution in the first round-bottom flask;

step (3): rising the temperature of the solution in the first round-bottom flask up to a first reaction temperature of 85° C., and then keeping the first reaction temperature for 48 hours; after that, a semi-finished product is produced in first round-bottom flask by 87% yield, and the semi-finished product is 1,1-bis (3-fluorobenzyl bromide) benzyl-4,4'-bipyridinium dibromide;

step (4): adding an aqueous solution of hexafluorophosphate into a second round-bottom flask;

step (5): rising the temperature of the solution in the second round-bottom flask up to 85° C., and then adding the obtained semi-finished product into the second round-bottom flask; and step (6): cooling the temperature of the solution in the second round-bottom flask down to 4° C.; after that, a product is produced in second round-bottom flask by 85% yield, and the product is 1,1-bis(3-fluorobenzyl bromide) benzyl-4,4'-bipyridinium dibromide.

Figure 1:
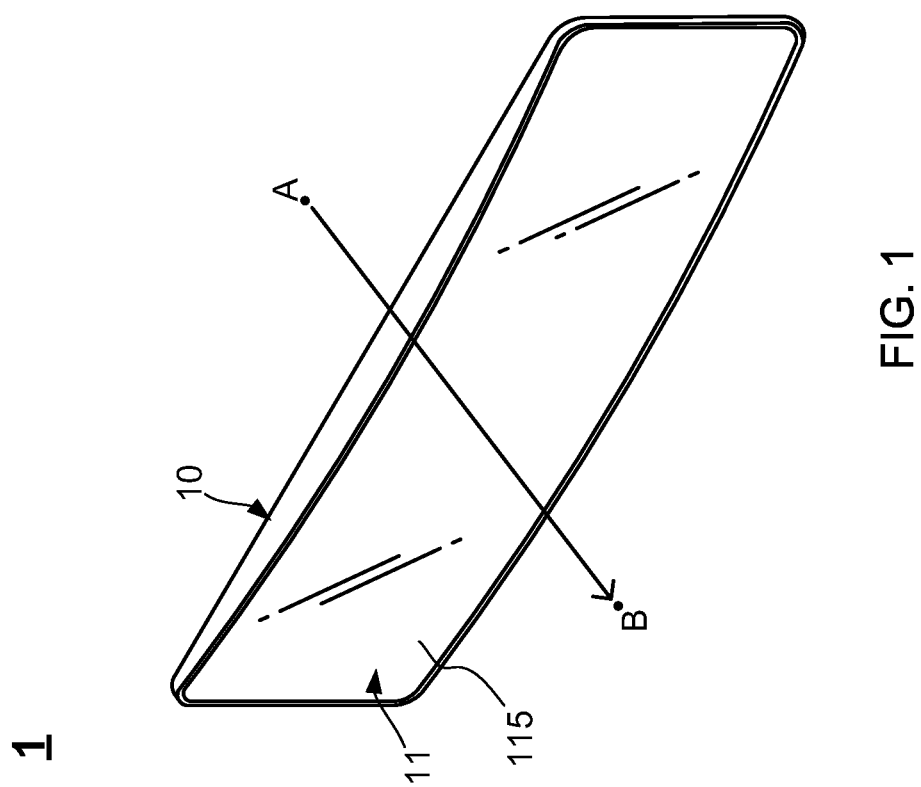
FIG. 1 shows a stereo diagram of an anti-dazzle mirror having a novel electrochromic material.

Continuously, the novel electrochromic material is applied in an automotive mirror, such that an anti-dazzle mirror is obtained. Please refer to FIG. 1, which illustrates a stereo diagram of the anti-dazzle mirror having the novel electrochromic material. As FIG. 1 shows, the anti-dazzle mirror 1 mainly comprises a mirror body 11 and a frame 10 for housing the mirror body 11. Continuously referring to FIG. 1, and please simultaneously refer to FIG. 2 and FIG. 3, where an exploded view and a cross-sectional view of the anti-dazzle mirror are respectively provided. Please read FIG. 2 and FIG. 3 according to the direction line formed by points A and B shown in FIG. 1. As FIG. 1, FIG. 2 and FIG. 3 show, the mirror body 11 comprises: a first transparent layer 111, a first electrode layer 112, an electrochromic layer 113, a second electrode layer 114, a second transparent layer 115, and a reflective film 116, wherein both the first transparent layer 111 and the second transparent layer 115 can be a transparent glass or a transparent acrylic.

Moreover, the first electrode layer 112 is disposed on the first transparent layer 111, and the electrochromic layer 113 comprising the novel electrochromic material is disposed on the first electrode layer 112. As the descriptions made above, the novel electrochromic material is a viologen compound having a specific chemical structure represented by the chemical formula (1). On the other hand, the second electrode layer 114 is disposed on the electrochromic layer 113, and the second transparent layer 115 is disposed on the second electrode layer 114. As the engineers skilled in automotive mirror designing and manufacturing technology field know, the top surface of the second transparent layer 115 is coated or covered with a reflective film 116, wherein the manufacturing material of the reflective film is selected from the group consisting of: aluminum (Al), silver (Ag), copper (Cu), chromium (Cr), and combinations thereof.

Before assembling the first transparent layer 111, the first electrode layer 112, the electrochromic layer 113, the second electrode layer 114, the second transparent layer 115, and the reflective film 116 to the mirror body 11, it needs to firstly adding the electrochromic material obtained from the step (6) and a phenazine compound in to a solvent of propylene carbonate by a mole ratio of 1:1, so as to produce an electrochromic material solution. Herein, it is worth explaining that the concentration of the novel electrochromic material in the electrochromic material solution is in a range from 250 mmol/L to 4000 mmol/L. Next, a seal agent 110 (as FIG. 2 shows) is used for making the first transparent layer 111 disposed with the first electrode layer 112 and the second transparent layer 115 disposed with the second electrode layer 114 attach to each other. Thus, the first transparent layer 111, the first electrode layer 112, the electrochromic layer 113, the second electrode layer 114, the second transparent layer 115, and the reflective film 116 are assembled to the mirror body 11.

Figure 2:
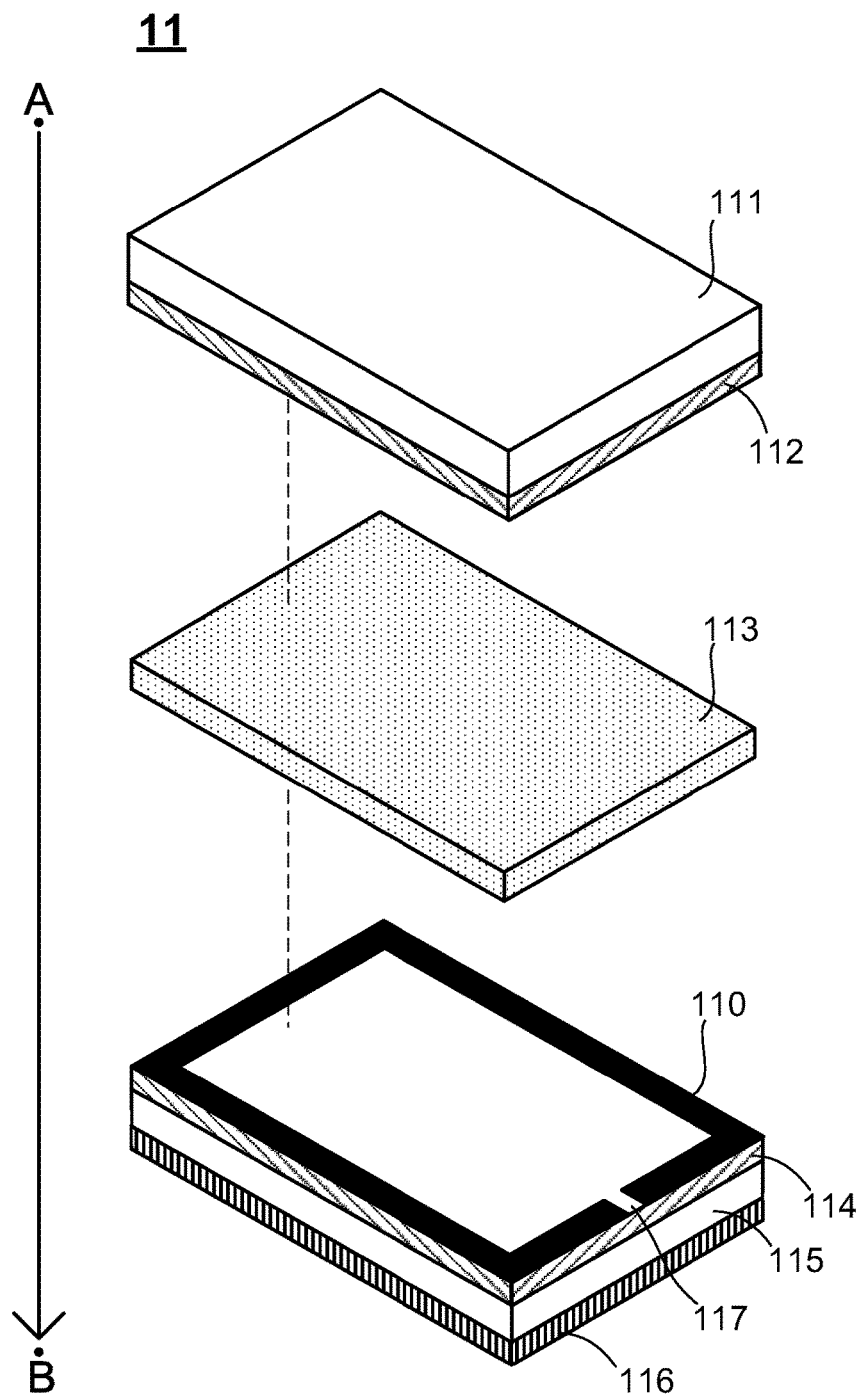
FIG. 2 shows an exploded view of the anti-dazzle mirror.
Figure 3:
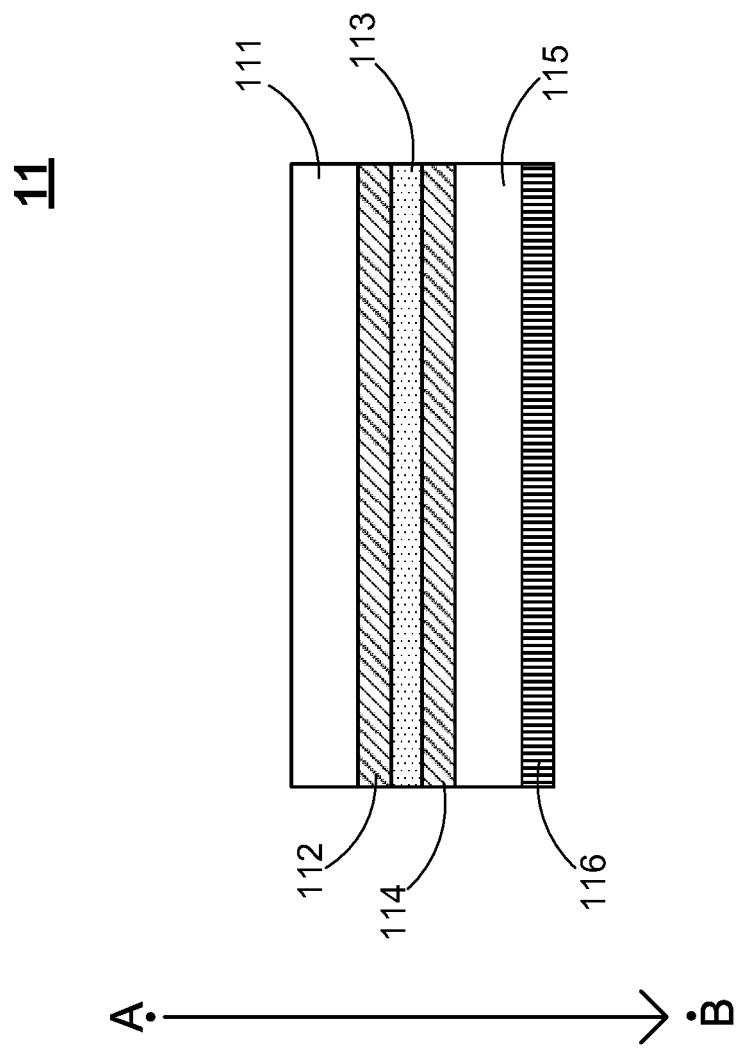
FIG. 3 shows a cross-sectional view of the anti-dazzle mirror.

From FIG. 2, it can find that the seal agent 110 is provided with a filling opening 117; so that, the electrochromic material solution is injected into an accommodating space enclosed by the seal agent 110, so as to form the electrochromic layer 113 located between the first electrode layer 112 and the second electrode layer 114. In the present invention, the seal agent 110 can be a light curing adhesive or a heat curing adhesive. Moreover, the seal agent 110 is mixed with a plurality of glass balls having a specific ball sizes. Because the ball size is in a range from 0.1 mm to 0.3 mm, the glass balls mixed in the seal agent 110 can be adopted for being spacers between the first electrode layer 112 and the second electrode layer 114 in order to guarantee the formation of the accommodating space. Eventually, after using a light curing adhesive to seal the filling opening 117 and subsequently using UV light to solidify the light curing adhesive, the product of the mirror body 11 is finished; and then, the final product of the anti-dazzle mirror 1 can be produced after embedded the mirror body 11 into the frame 10. After obtaining the anti-dazzle mirror 1 proposed by the present invention, the reflectivity and color changing speed of the anti-dazzle mirror 1 is measured and recorded in following Table (2) and Table (3).

TABLE 2

| Measurement items | Results |
|---|---|
| Reflectivity obtained without changing the electrochromic material's color | 59.81% |
| Reflectivity obtained without changing the electrochromic material's color (measured after treating the anti-dazzle mirror with a high-temperature storage of 90° C. for 8 hours) | 59.13% |
| Reflectivity obtained without changing electrochromic material's color (measured after treating the anti-dazzle mirror with a low-temperature storage of −40° C. for 8 hours) | 58.24% |
| Reflectivity obtained without changing the electrochromic material's color (measured after treating the anti-dazzle mirror with a storage with high-temperature of 60° C. and high-humidity of 90% for 8 hours) | 57.94% |
| Reflectivity obtained without changing the electrochromic material's color (measured after treating the anti-dazzle mirror with 60000-time cycling test by DC 1.2 V) | 59.47% |

TABLE 3

| Measurement items | Results |
|---|---|
| Reflectivity obtained after changing the electrochromic material's color | 7.13% |
| Color changing speed (from 55% to 10%) | 2 s |
| Color changing speed (from 10% to 55%) | 7 s |
| Reflectivity obtained after changing the electrochromic material's color (measured after treating the anti-dazzle mirror with a high-temperature storage of 90° C. for 8 hours) | 8.90% |
| Reflectivity obtained after changing electrochromic material's color (measured after treating the anti-dazzle mirror with a low-temperature storage of −40° C. for 8 hours) | 9.40% |
| Reflectivity obtained after changing the electrochromic material's color (measured after treating the anti-dazzle mirror with a storage with high-temperature of 60° C. and high-humidity of 90% for 8 hours) | 9.28% |
| Reflectivity obtained after changing the electrochromic material's color (measured after treating the anti-dazzle mirror with 60000-time cycling test by DC 1.2 V) | 9.35% |

Therefore, from above-presented Table (2) and Table (3), the engineers skilled in designing and manufacturing electrochromic materials can easily find that, the proposed anti-dazzle mirror 1 having the novel electrochromic material performs a good anti-dazzle effect for automobile drivers because the reflectivity of the anti-dazzle mirror 1 measured after changing electrochromic material's color is down to 7.13%. On the other hand, after comparing Table (3) with Table (1), it can also find that the reflectivity of the anti-dazzle mirror 1 measured after changing the novel electrochromic material's color is lower than the reflectivity of the automotive mirror measured after changing the improved electrochromic material's (disclosed by Taiwan patent number I265972) color.

Therefore, through above descriptions, the novel electrochromic material and the anti-dazzle mirror having the novel electrochromic material provided by the present invention has been introduced completely and clearly; in summary, the present invention includes the advantages of:

(1) Comparing to conventional electrochromic materials disclosed by Taiwan patent number I265972 showing a primary drawback of high manufacturing cost due to low synthetic yield, the inventors of the present invention modulate the chemical structure of a traditional viologen compound so as to develop a novel electrochromic material performing an excellent advantage of low manufacturing cost resulted from high recovery rate.

(2) Moreover, differing from the conventional electrochromic device (ECD) taught by Taiwan patent number I265972, the inventors of the present invention also propose an anti-dazzle mirror having the novel electrochromic material, wherein the proposed anti-dazzle mirror shows an outstanding reflectivity performance.

The above description is made on embodiments of the present invention. However, the embodiments are not intended to limit scope of the present invention, and all equivalent implementations or alterations within the spirit of the present invention still fall within the scope of the present invention.

What is claimed is:

1. An electrochromic material, being a viologen compound having a specific chemical structure represented by following chemical formula (1):

[chemical formula (1)]

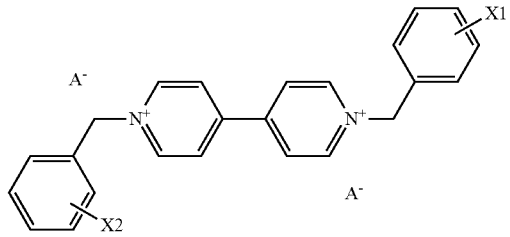

wherein both X1 and X2 in the chemical formula (1) are a halogen, and $A^-$ being a compensatory ion.

2. The electrochromic material of claim 1, wherein the compensatory ion is selected from the group consisting of: $BF_4^-$, $PF_6^-$, $AsF_6^-$, $ClO_4^-$, $CH_3COO^-$, $CH_3(C_6H_4)SO_3^-$, and $(CF_3SO_2)_2N^-$.

3. The electrochromic material of claim 1, wherein the compensatory ion is a halogen ion.

4. An anti-dazzle mirror, comprising:
    a mirror body, comprising:
        a first transparent layer;
        a first electrode layer, being disposed on the first transparent layer;
        an electrochromic layer, being disposed on the first electrode layer and comprising an electrochromic material;
        a second electrode layer, being disposed on the electrochromic layer;
        a second transparent layer, being disposed on the second electrode layer; and
        a reflective film, covering the second transparent layer, wherein the electrochromic material is a viologen compound having a specific chemical structure represented by following chemical formula (1):

[chemical formula (1)]

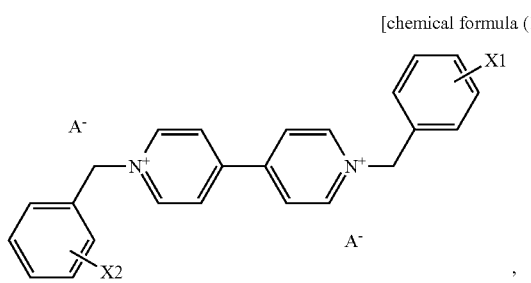

wherein both X1 and X2 in the chemical formula (1) are a halogen, and A⁻ being a compensatory ion.

5. The anti-dazzle mirror of claim 4, further comprising a frame for housing the mirror body.

6. The anti-dazzle mirror of claim 4, wherein the compensatory ion is selected from the group consisting of: $BF_4^-$, $PF_6^-$, $AsF_6^-$, $ClO_4^-$, $CH_3COO^-$, $CH_3(C_6H_4)SO_3^-$, and $(CF_3SO_2)_2N^-$.

7. The anti-dazzle mirror of claim 4, wherein the compensatory ion is a halogen ion.

8. The anti-dazzle mirror of claim 4, wherein both the first transparent layer and the second transparent layer are selected from the group consisting of: transparent glass and transparent acrylic.

9. The anti-dazzle mirror of claim 4, wherein the manufacturing material of the reflective film is selected from the group consisting of: aluminum (Al), silver (Ag), copper (Cu), chromium (Cr), and combination thereof.

10. The anti-dazzle mirror of claim 4, wherein a seal agent is used for attaching the first transparent layer disposed with the first electrode layer to the second transparent layer disposed with the second electrode layer.

11. The anti-dazzle mirror of claim 10, wherein the seal agent is selected from the group consisting of: light curing adhesive and heat curing adhesive.

* * * * *